United States Patent
Fujimura

(10) Patent No.: US 9,924,925 B2
(45) Date of Patent: Mar. 27, 2018

(54) ULTRASOUND TRANSDUCER AND ULTRASOUND PROBE

(71) Applicant: OLYMPUS CORPORATION, Tokyo (JP)

(72) Inventor: Takanao Fujimura, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/482,062

(22) Filed: Apr. 7, 2017

(65) Prior Publication Data

US 2017/0209120 A1    Jul. 27, 2017

Related U.S. Application Data

(63) Continuation of application No. PCT/JP2016/062085, filed on Apr. 15, 2016.

(30) Foreign Application Priority Data

Apr. 30, 2015   (JP) .................................. 2015-092991

(51) Int. Cl.
*A61B 8/00* (2006.01)
*A61B 8/12* (2006.01)
(Continued)

(52) U.S. Cl.
CPC ........ *A61B 8/4483* (2013.01); *A61B 1/00045* (2013.01); *A61B 1/06* (2013.01);
(Continued)

(58) Field of Classification Search
None
See application file for complete search history.

(56) References Cited

U.S. PATENT DOCUMENTS

| 5,655,539 A * | 8/1997 | Wang .................. A61B 8/4281 600/472 |
| 2007/0164632 A1 | 7/2007 | Adachi et al. |

(Continued)

FOREIGN PATENT DOCUMENTS

| JP | 2008-245705 A | 10/2008 |
| JP | 2015-070473 A | 4/2015 |

(Continued)

OTHER PUBLICATIONS

International Search Report dated Jul. 5, 2016 issued in PCT/JP2016/062085.

*Primary Examiner* — James Kish
(74) *Attorney, Agent, or Firm* — Scully, Scott, Murphy & Presser, P.C.

(57) ABSTRACT

Provided is an ultrasound transducer for irradiating a subject with ultrasound and receiving an ultrasound echo reflected from the subject. The ultrasound transducer includes a plurality of piezoelectric elements configured to emit ultrasound according to input of an electric signal and convert ultrasound incident from outside into an electric signal, and a mask portion provided between the plurality of piezoelectric elements and a radiation surface of the ultrasound on the ultrasound transducer. The mask portion is configured to: mask any divided region among a plurality of divided regions obtained by dividing an elevation direction orthogonal to a plane parallel to a scanning direction of the ultrasound; reflect the ultrasound in a direction different from a propagation direction of the ultrasound on the masked division region; and allow the ultrasound to pass in the propagation direction in the plurality of divided regions except the masked divided region.

5 Claims, 15 Drawing Sheets

(51) Int. Cl.
*H04R 17/00* (2006.01)
*H04R 19/00* (2006.01)
*A61B 1/00* (2006.01)
*A61B 1/06* (2006.01)
*A61B 8/14* (2006.01)
*A61B 1/307* (2006.01)

(52) U.S. Cl.
CPC ............... *A61B 8/12* (2013.01); *A61B 8/14* (2013.01); *A61B 8/4444* (2013.01); *A61B 8/461* (2013.01); *H04R 17/00* (2013.01); *H04R 19/00* (2013.01); *A61B 1/307* (2013.01)

(56) References Cited

U.S. PATENT DOCUMENTS

2008/0139946 A1 6/2008 Adachi et al.
2011/0319768 A1 12/2011 Saito
2015/0094596 A1 4/2015 Kiyose et al.

FOREIGN PATENT DOCUMENTS

WO    WO 2005/120130 A1    12/2005
WO    WO 2010/100921 A1    9/2010

* cited by examiner

ULTRASOUND TRANSDUCER AND ULTRASOUND PROBE

CROSS REFERENCES TO RELATED APPLICATIONS

This application is a continuation of PCT international application Ser. No. PCT/JP2016/062085, filed on Apr. 15, 2016 which designates the United States, incorporated herein by reference, and which claims the benefit of priority from Japanese Patent Application No. 2015-092991, filed on Apr. 30, 2015, incorporated herein by reference.

BACKGROUND

1. Technical Field

The disclosure relates to an ultrasound transducer and an ultrasound probe for emitting ultrasound to an observation target, receiving an ultrasound echo reflected from the observation target, converting the received ultrasound echo into an echo signal, and outputting the converted signal.

2. Related Art

Ultrasound is applied in order to observe characteristics of living tissues or materials as an observation target. To be specific, the ultrasound transducer transmits the ultrasound to the observation target and receives an ultrasound echo reflected from the observation target, and the ultrasound observation apparatus can acquire information on the characteristics of the observation target by performing predetermined signal processing on the received ultrasound echo.

The ultrasound transducer includes a plurality of piezoelectric elements, each of which converts an electrical pulse signal into an ultrasound pulse (acoustic pulse) and emits the converted signal to the observation target, and further, converts the ultrasound echo reflected from the observation target into an electrical echo signal expressed by a voltage change and outputs the converted signal. For example, the ultrasound echo is acquired from the observation target by arraying the plurality of piezoelectric elements in a predetermined direction, electronically switching an element relating to transmission and reception, or causing a delay for transmission and reception of a piezoelectric body of each of the ultrasound transducers. The ultrasound transducer, which transmits the ultrasound in the one predetermined direction and acquires the ultrasound echo reflected from the observation target in this manner, is called a 1-D array ultrasound transducer.

As the ultrasound transducer, 2-D array ultrasound transducer in which a plurality of piezoelectric elements is arranged in a matrix and two directions intersecting each other are set as scanning directions has been known in addition to the above-described 1-D array type (for example, see JP 2008-245705 A). For example, the 2-D array ultrasound transducer can acquire an ultrasound echo in an elevation direction which is orthogonal to the scanning direction of the 1-D array ultrasound transducer. The 2-D array ultrasound transducer can acquire a plurality of ultrasound images (sectional images) in the elevation direction. Thus, when the ultrasound transducer is provided at a distal end portion of an endoscope and a position of a puncture needle protruding from the distal end portion of the endoscope is confirmed while examining an inside of an observation target, for example, it is possible to confirm an inclination direction of the puncture needle from the plurality of ultrasound images even if a protruding direction of the puncture needle is inclined with respect to the scanning direction.

SUMMARY

In some embodiments, provided is an ultrasound transducer for irradiating a subject with ultrasound and receiving an ultrasound echo reflected from the subject. The ultrasound transducer includes a plurality of piezoelectric elements configured to emit ultrasound according to input of an electric signal and convert ultrasound incident from outside into an electric signal, and a mask portion provided between the plurality of piezoelectric elements and a radiation surface of the ultrasound on the ultrasound transducer. The mask portion is configured to: mask any divided region among a plurality of divided regions obtained by dividing an elevation direction orthogonal to a plane parallel to a scanning direction of the ultrasound; reflect the ultrasound in a direction different from a propagation direction of the ultrasound on the masked division region; and allow the ultrasound to pass in the propagation direction in the plurality of divided regions except the masked divided region.

In some embodiments, an ultrasound probe includes the ultrasound transducer at a distal end of the ultrasound probe.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, modes for carrying out the present invention (hereinafter, referred to as embodiment(s)) will be described with reference to the drawings. The present invention is not limited to the embodiments to be described below. The same reference signs are used to designate the same elements throughout the drawings.

First Embodiment

Figure 1:
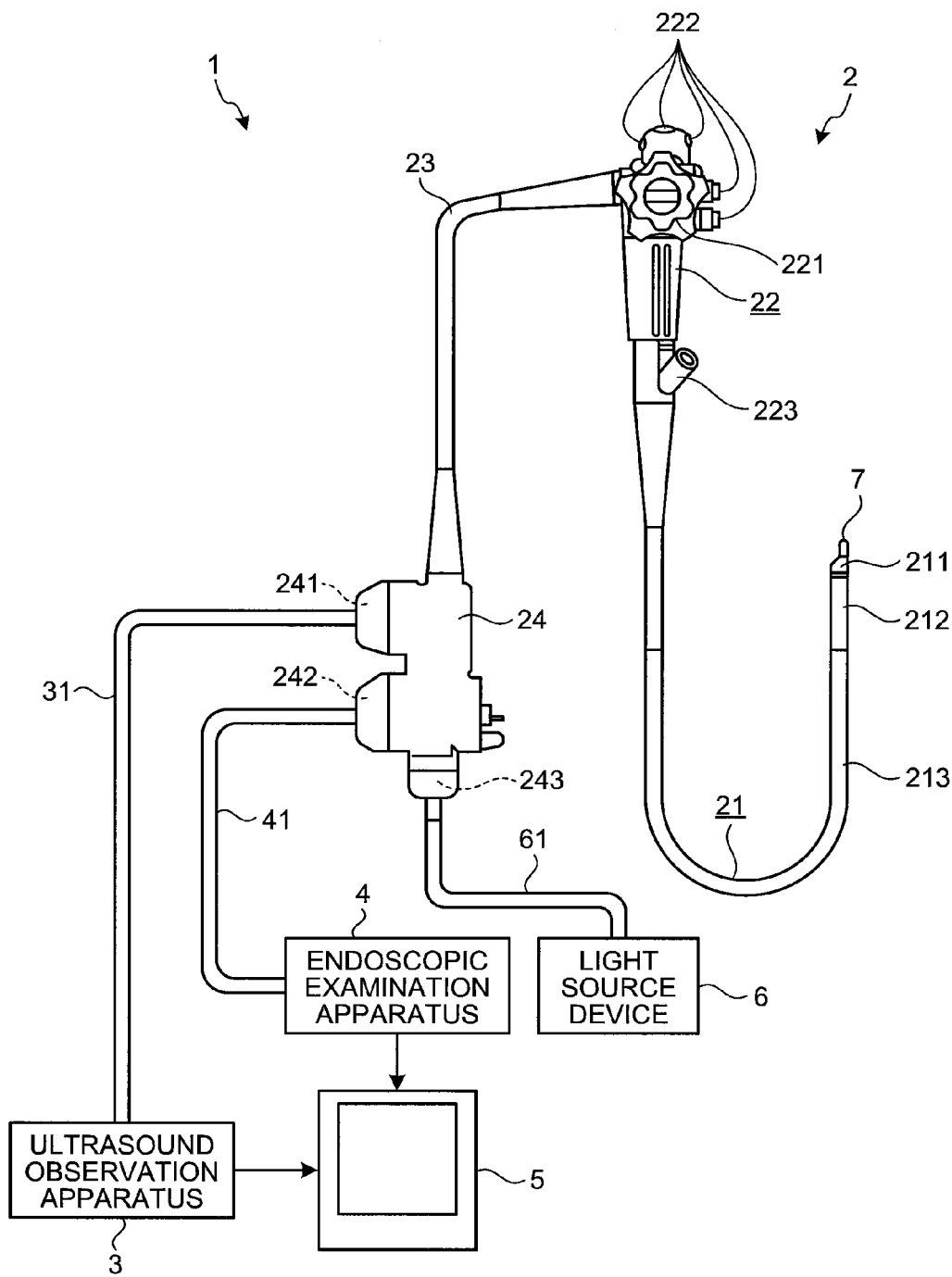
FIG. 1 is a diagram schematically illustrating an endoscopic system according to a first embodiment of the present invention.

FIG. 1 is a diagram schematically illustrating an endoscopic system according to a first embodiment of the present invention. An endoscopic system 1 is a system that performs ultrasound diagnosis inside a subject such as human using an ultrasound endoscope. As illustrated in FIG. 1, the endoscopic system 1 includes an ultrasound endoscope 2, an ultrasound observation apparatus 3, an endoscopic examination apparatus 4, a display device 5, and a light source device 6.

The ultrasound endoscope 2 includes an ultrasound transducer, which converts an electrical pulse signal received from the ultrasound observation apparatus 3 into an ultrasound pulse (acoustic pulse) and emits the converted signal to the subject, and converts the ultrasound echo reflected from the subject into an electrical echo signal expressed in a voltage change and outputs the converted signal, at a distal end portion thereof. A configuration of the ultrasound transducer will be described later.

The ultrasound endoscope 2 generally includes an imaging optical system and an image sensor so that it is possible to perform imaging of digestive tracts or respiratory organs when being inserted into the digestive tract (an esophagus, a stomach, a duodenum, or a colon) or the respiratory organ (a trachea or a bronchial tube) of the subject. In addition, it is possible to perform imaging of adjacent organs (a pancreas, a gall bladder, a biliary duct, a biliary tract, a lymph node, a mediastinum, a blood vessel or the like) using the ultrasound. In addition, the ultrasound endoscope 2 includes a light guide that guides illumination light with which the subject is irradiated at the time of optical imaging. The light guide has a distal end portion that reaches a distal end of an insertion portion of the ultrasound endoscope 2 inserted into the subject, and a proximal end portion that is connected to the light source device 6 which generates the illumination light.

As illustrated in FIG. 1, the ultrasound endoscope 2 includes an insertion portion 21, an operating unit 22, a universal cable 23, and a connector 24. The insertion portion 21 is a portion that is inserted inside the subject. As illustrated in FIG. 1, the insertion portion 21 includes an ultrasound transducer 7 provided on the distal end side, a rigid member 211 connected to a proximal end side of the ultrasound transducer 7, a bent portion 212, which is connected to a proximal end side of the rigid member 211 to be bendable, and a flexible tube portion 213 which is connected to a proximal end side of the bent portion 212 and has flexibility. Here, the light guide to transmit the illumination light supplied from the light source device 6 and a plurality of signal cables to transmit various signals are wired, although not illustrated in detail, and a treatment tool passage, which allows a treatment tool to be inserted therethrough, is formed inside the insertion portion 21.

The ultrasound transducer 7 may employ any one among a convex transducer, a linear transducer, and a radial transducer. In the first embodiment, the ultrasound endoscope 2 in which the plurality of piezoelectric elements, each serving as the ultrasound transducer 7, is provided in an array, and scanning is electronically performed by electronically switching a piezoelectric element relating to transmission and reception or causing a delay in each piezoelectric element. However, the ultrasound transducer 7 may be configured to mechanically perform scanning. The configuration of the ultrasound transducer 7 will be described later.

Figure 2:
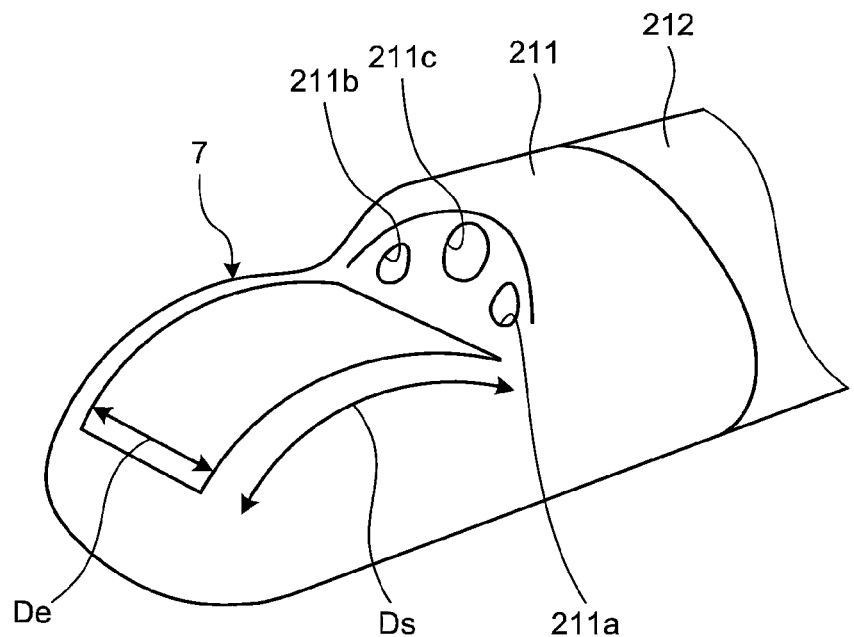
FIG. 2 is a perspective view schematically illustrating a configuration of a distal end of an insertion portion of an ultrasound endoscope according to the first embodiment of the present invention.

FIG. 2 is a perspective view schematically illustrating a configuration of the distal end of the insertion portion of the ultrasound endoscope according to the first embodiment. As illustrated in FIG. 2, the rigid member 211 includes an illumination lens 211a which condenses the illumination light and emits the light to the outside, an objective lens 211b which forms a part of an imaging optical system and introduces the light from the outside, and a treatment tool protrusion port 211c which communicates with the treatment tool passage formed inside the insertion portion 21 and causes the treatment tool to protrude from the distal end of the insertion portion 21.

The operating unit 22 is a portion that is connected to a proximal end side of the insertion portion 21 and receives various operations from a doctor or the like. As illustrated in FIG. 1, the operating unit 22 includes a bending knob 221 to perform a bending operation of the bent portion 212 and a plurality of operating members 222 to perform various operations. In addition, a treatment tool insertion port 223, which communicates with the treatment tool passage and through which the treatment tool is inserted into the treatment tool passage, is formed in the operating unit 22.

The universal cable 23 is a cable that extends from the operating unit 22 and is formed by arranging a plurality of signal cables to transmit various signals, an optical fiber to transmit the illumination light supplied from the light source device 6, and the like.

The connector 24 is provided at a distal end of the universal cable 23. Further, the connector 24 includes first to third connector portions 241 to 243 which are connected with an ultrasound cable 31, a video cable 41, and an optical fiber cable 61, respectively.

The ultrasound observation apparatus 3 is electrically connected to the ultrasound endoscope 2 via the ultrasound cable 31 (FIG. 1), and outputs a pulse signal to the ultrasound endoscope 2 via the ultrasound cable 31 and an echo signal from the ultrasound endoscope 2 is input thereto. Further, the ultrasound observation apparatus 3 performs predetermined processing on the echo signal to generate an ultrasound image.

The endoscopic examination apparatus 4 is electrically connected to the ultrasound endoscope 2 via the video cable 41 (FIG. 1), and an image signal from the ultrasound endoscope 2 is input thereto via the video cable 41. Further, the endoscopic examination apparatus 4 performs predetermined processing on the image signal to generate an endoscopic image.

The display device 5 is configured using a liquid crystal or organic electro luminescence (EL), or the like, and displays the ultrasound image generated by the ultrasound observation apparatus 3, the endoscopic image displayed by the endoscopic examination apparatus 4, and the like.

The light source device 6 is connected to the ultrasound endoscope 2 via the optical fiber cable 61 (FIG. 1) and supplies the illumination light to illuminate the inside of the subject to the ultrasound endoscope 2 via the optical fiber cable 61.

Figure 3:
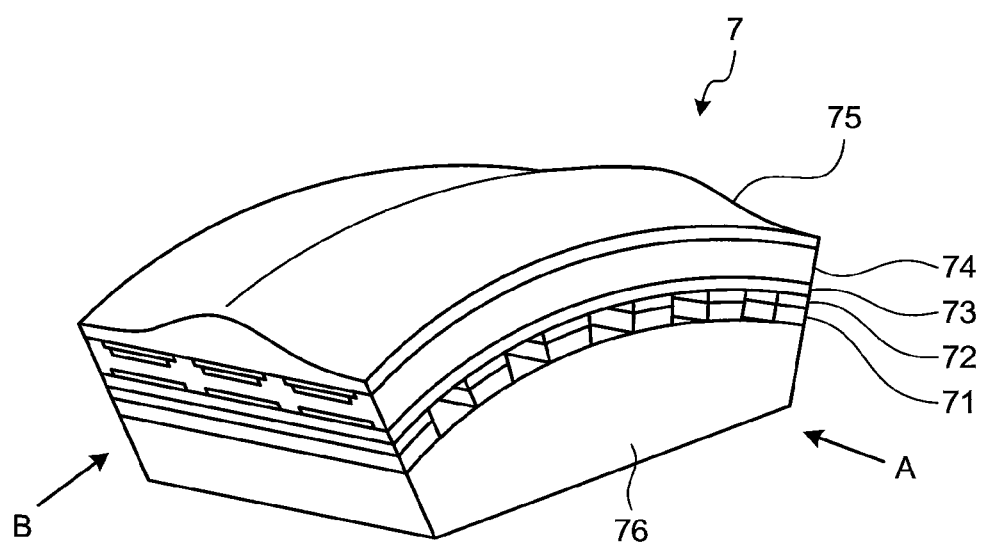
FIG. 3 is a perspective view schematically illustrating a configuration of an ultrasound transducer according to the first embodiment of the present invention.
Figure 4:
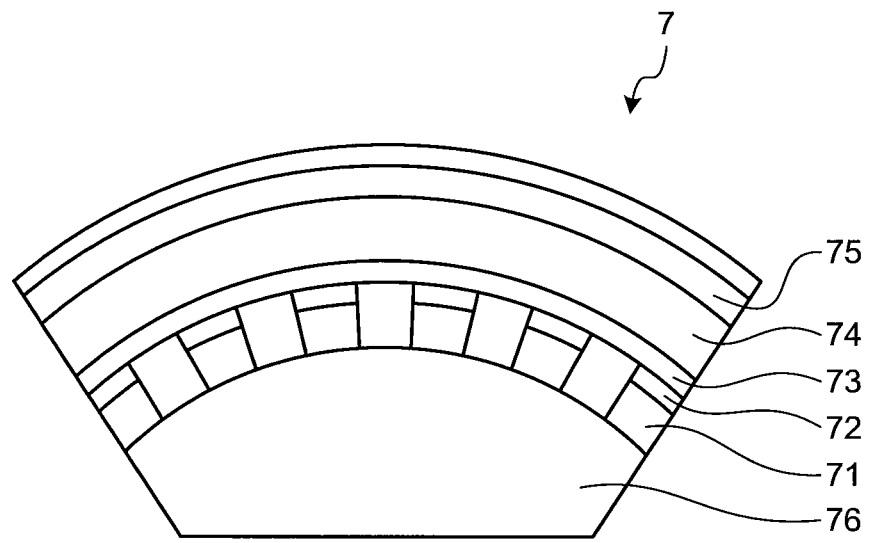
FIG. 4 is a plan view schematically illustrating the configuration of the ultrasound transducer when seen in an arrow A direction illustrated in FIG. 3.
Figure 5:
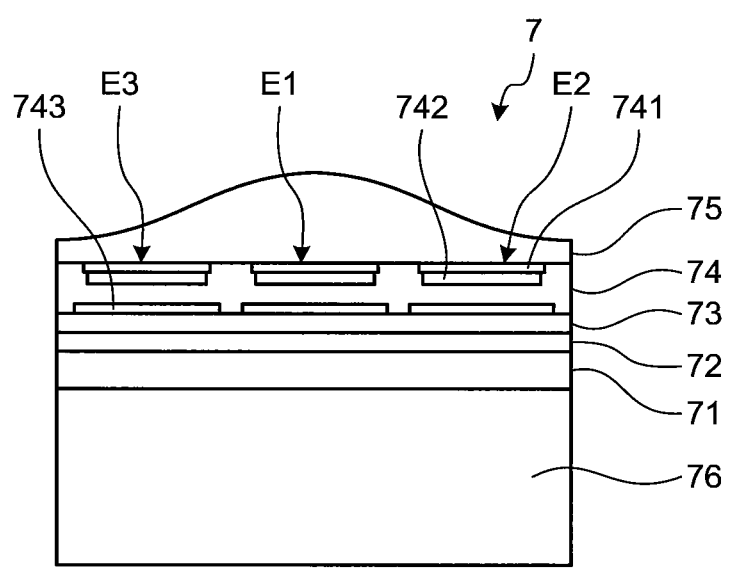
FIG. 5 is a plan view schematically illustrating the configuration of the ultrasound transducer when seen in an arrow B direction illustrated in FIG. 3.
Figure 6:
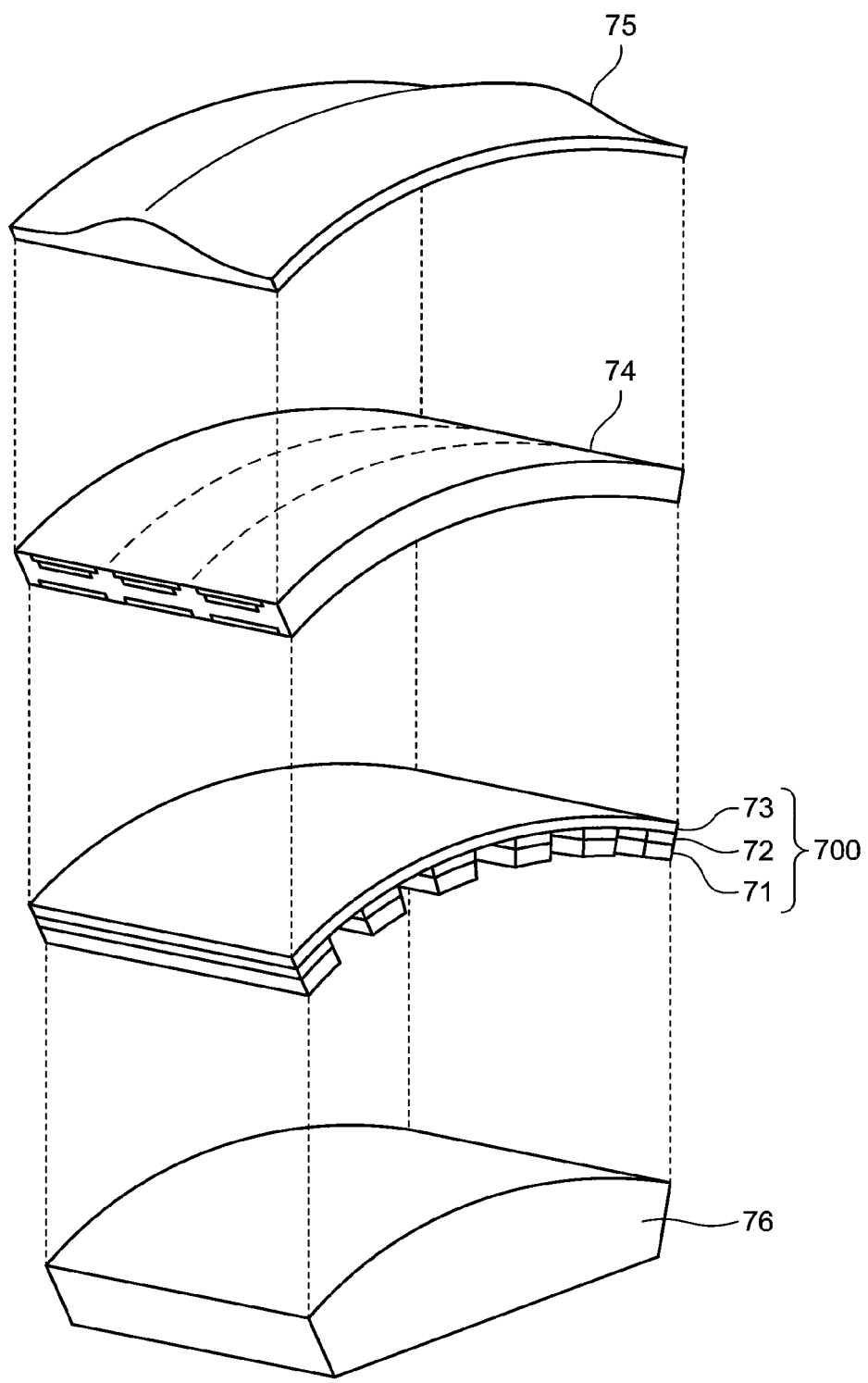
FIG. 6 is an exploded perspective view schematically illustrating the configuration of the ultrasound transducer according to the first embodiment of the present invention.

Next, the configuration of the ultrasound transducer 7 provided at the distal end of the insertion portion 21 will be described with reference to FIGS. 2 to 6. FIG. 3 is a perspective view schematically illustrating the configuration of the ultrasound transducer according to the first embodiment. FIG. 4 is a plan view schematically illustrating the configuration of the ultrasound transducer when seen in an arrow A direction illustrated in FIG. 3. FIG. 5 is a plan view schematically illustrating the configuration of the ultrasound transducer when seen in an arrow B direction illustrated in FIG. 3. FIG. 6 is an exploded perspective view schematically illustrating the configuration of the ultrasound transducer according to the first embodiment. FIGS. 3 and 4 illustrate a case where six piezoelectric elements 71 are arranged side by side. However, the configuration of the ultrasound transducer 7 is simplified in the drawings in order for description, and the number of piezoelectric elements that are actually arranged is not limited thereto. In the first embodiment, the ultrasound transducer 7 is a convex-type ultrasound transducer illustrated in FIG. 2 with an one-dimensional array (1-D array) in which the plurality of piezoelectric elements 71 is arrayed in line. In other words, the plurality of piezoelectric elements 71 is arranged in an outer surface that forms a curved surface of the ultrasound transducer 7 in the ultrasound transducer 7 according to the first embodiment.

The ultrasound transducer 7 includes the plurality of piezoelectric elements 71, each of which has a prismatic shape and is aligned side by side in the longitudinal direction, a plurality of first acoustic matching layers 72, each of which is provided on the outer surface side of the ultrasound transducer 7 with respect to the piezoelectric element 71, a second acoustic matching layer 73 provided on the opposite side to a side of the first acoustic matching layer 72, the side in contact with the piezoelectric element 71, a mask portion 74 provided on the opposite side to a side of the second acoustic matching layer 73, the side in contact with the first acoustic matching layer 72, an acoustic lens 75 provided on the opposite side to a side of the mask portion 74, the side in contact with the second acoustic matching layer 73, and a backing material 76 provided on the opposite side to a side of the piezoelectric element 71, the side in contact with the first acoustic matching layer 72. It is configured in the first embodiment such that the first acoustic matching layer 72 is provided for each of the piezoelectric elements 71, the second acoustic matching layer 73, the mask portion 74, the acoustic lens 75, and the backing material 76 collectively cover the plurality of piezoelectric elements 71 and first acoustic matching layers 72. The ultrasound transducer 7 may be a type of using the single piezoelectric element 71 as an output unit or a type of using the plurality of piezoelectric elements 71 as an output unit. As illustrated in FIG. 2, a longitudinal direction of the piezoelectric element 71 will be referred to as an elevation direction De, and an array direction of the piezoelectric element 71 will be referred to as a scanning direction Ds, hereinafter. In addition, a piezoelectric element unit 700 is configured using the piezoelectric element 71, the first acoustic matching layer 72, and the second acoustic matching layer 73.

The piezoelectric element 71 converts an electrical pulse signal into an ultrasound pulse (acoustic pulse) and emits the converted signal to a subject, and further, converts an ultrasound echo reflected from the subject into an electrical echo signal expressed by a voltage change and outputs the converted signal. The piezoelectric element 71 is provided with an electrode for input and output of a signal on a main surface on the backing material 76 side, and an electrode for grounding on a main surface of the piezoelectric element 71 on the first acoustic matching layer 72 side. Each of the electrodes is formed using a metal material having conductivity or a resin material.

The piezoelectric element 71 is formed using a PZT ceramic material, a PMN-PT single crystal, a PMN-PZT single crystal, a PZN-PT single crystal, a PIN-PZN-PT single crystal, or a relaxor-based material. The PMN-PT single crystal is an abbreviation of a solid solution of lead magnesium niobate and lead titanate. The PMN-PZT single crystal is an abbreviation of a solid solution of lead magnesium niobate and lead zirconate titanate. The PZN-PT single crystal is an abbreviation of a solid solution of lead zinc niobate and lead titanate. The PIN-PZN-PT single crystal is an abbreviation of a solid solution of lead indium niobate, lead zinc niobate, and lead titanate. The relaxor-based material is a generic term of a three-component piezoelectric material formed by adding lead complex perovskite, which is a relaxor material, to lead zirconate titanate (PZT) in order to increase a piezoelectric constant or a dielectric constant. The lead complex perovskite is expressed by $Pb(B1, B2)O_3$ in which B1 is any of magnesium, zinc, indium and scandium and B2 is any of niobium, tantalum and tungsten. These materials provide an excellent piezoelectric effect. Thus, a value of electrical impedance can be made low even though the piezoelectric elements are downsized, which is favorable from the viewpoint of impedance matching between the piezoelectric element and a thin-film electrode provided on the piezoelectric element 71.

The first acoustic matching layer 72 and the second acoustic matching layer 73 perform matching of an acoustic impedance between the piezoelectric element 71 and the observation target in order to cause a sound (ultrasound) to be efficiently transmitted between the piezoelectric element 71 and the observation target. The first acoustic matching layer 72 and the second acoustic matching layer 73 are made of materials different from each other. In the first embodiment, the two acoustic matching layers (the first acoustic matching layer 72 and the second acoustic matching layer 73) are provided. However, one acoustic matching layer or three or more acoustic matching layers may be provided according to characteristics of the piezoelectric element 71 and the observation target. In addition, the acoustic matching layer is not necessarily provided and an ultrasound transducer having no acoustic matching layer may be configured as long as the matching of the acoustic impedance with the observation target is obtained.

The mask portion 74 regulates passage of the ultrasound in the elevation direction De of the ultrasound transducer 7 by masking a part of the piezoelectric element 71 in the elevation direction De. In other words, the mask portion 74 is configured to mask any divided region among a plurality of divided regions, obtained by dividing the elevation direction De, reflect the ultrasound in a direction different from a propagation direction of the ultrasound on the masked divided region, and allow the passage of the ultrasound in the propagation direction in the plurality of divided regions except the masked divided region.

Figure 7:
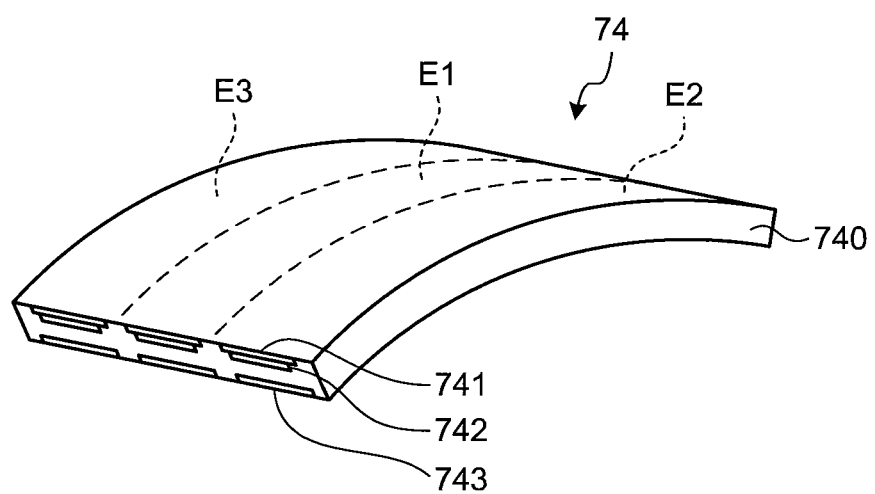
FIG. 7 is a schematic diagram illustrating a configuration of main parts of the ultrasound transducer according to the first embodiment of the present invention.

FIG. 7 is a schematic diagram illustrating a configuration of main parts of the ultrasound transducer according to the first embodiment, and is a diagram for describing a configuration of the mask portion 74. The mask portion 74 includes a sheet-shaped main body portion 740, formed using a material that allows ultrasound to pass therethrough, and is provided between the second acoustic matching layer 73 and the acoustic lens 75. The main body portion 740 includes three electret portions 741, which are provided on one surface, have a rectangular shape, and maintain electric polarization to generate an electric field, three hollow portions 742 forming strip-shaped hollow spaces in accordance with arrangement of the electret portion 741, and three counter electrodes 743 which are provided on the other surface so as to face the electret portion 741 and have a strip shape. The hollow portion 742 is filled with gas (air).

The electret portion 741 is implemented using a rectangular-shaped electret (electric stone) that is made of fluororesin such as Teflon (registered trademark) or polyethylene terephthalate (PET), and maintains the electric polarization to generate the electric field. In the first embodiment, the hollow portion 742 side (the counter electrode 743 side) is positively charged.

Whether to apply a charge to the counter electrode 743 is switched under control of a control unit (not illustrated). The counter electrode 743 is negatively charged when a charge is applied thereto, for example. The counter electrode 743 is formed using a material that can pass at least ultrasound.

When any of the three counter electrodes 743 is electrically charged, the mask portion 74 eliminates the hollow space present in a traveling direction of ultrasound to enable the passage of the ultrasound. To be specific, when three mask structures of the electret portion 741, the hollow portion 742, and the counter electrode 743 are arrayed in the elevation direction De in the ultrasound transducer 7, the mask portion 74 divides the region to be masked into three regions in the elevation direction De (divided regions E1 to E3). Thus, the ultrasound transducer 7 emits ultrasound with a partial region in the elevation direction De that has been masked. When the counter electrode 743 is electrically charged in any divided region among the three divided regions E1 to E3, the electret portion 741 enters into the hollow portion 742 and is brought into contact with a bottom surface, and the ultrasound can pass the divided region according to the corresponding counter electrode 743. For example, when the counter electrode 743 in the divided region E1 is electrically charged, the ultrasound is emitted only from the divided region E1.

Figure 8:
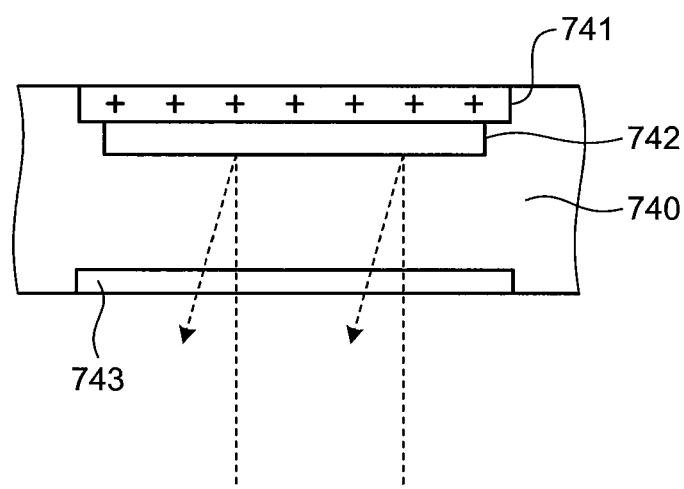
FIG. 8 is a diagram for describing propagation of ultrasound in the ultrasound transducer according to the first embodiment of the present invention.
Figure 9:
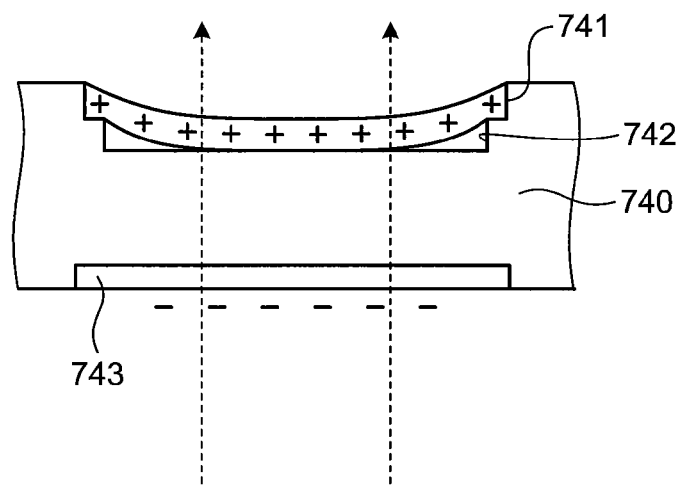
FIG. 9 is a diagram for describing propagation of ultrasound in the ultrasound transducer according to the first embodiment of the present invention.

Here, the masking processing performed by the mask portion 74 of the ultrasound transducer 7 will be described with reference to FIGS. 8 and 9. FIG. 8 is a diagram for describing propagation of ultrasound in the ultrasound transducer according to the first embodiment and illustrating a state in which the counter electrode 743 has no charge. FIG. 9 is a diagram for describing propagation of ultrasound in the ultrasound transducer according to the first embodiment and illustrating a state in which the counter electrode 743 is electrically charged.

The mask portion 74 blocks the passage of the ultrasound when the counter electrode 743 has no charge since the gas is present between the electret portion 741 and the counter electrode 743 due to the hollow portion 742 as illustrated in FIG. 8 (a dashed arrow in FIG. 8). At this time, the ultrasound is reflected from the hollow portion 742 (gas) toward a direction different from the propagation direction of the ultrasound.

The mask portion 74 enables the passage of the ultrasound when the counter electrode 743 is electrically charged since the electret portion 741 is attracted to the counter electrode 743 which has been negatively charged, to enter into the hollow portion 742 and be brought into contact with the bottom of the hollow portion 742 as illustrated in FIG. 9 (a dashed arrow in FIG. 9).

In this manner, the passage of the ultrasound using the mask portion 74 is controlled by the application of the charge to the counter electrode 743. It is possible to emit the ultrasound from a desired region by controlling the application of the charge to the divided regions E1 to E3. In addition, conversely, it is possible to control a reception region of the ultrasound echo by the application of the charge.

Returning to FIGS. 3 to 6, the acoustic lens 75 is formed using silicone, polymethylpentene, epoxy resin, polyetherimide, or the like, has one surface formed in a convex shape or a concave shape and serving a function of narrowing the ultrasound, emits the ultrasound passed through the mask portion 74 to the outside or take the ultrasound echo from the outside. The acoustic lens 75 is also provided in an arbitrary manner, and it may be configured without the acoustic lens 75.

The backing material 76 attenuates unnecessary ultrasound vibration that is caused by the operation of the piezoelectric element 71. The backing material 76 is formed using a material with a high attenuation rate, for example, epoxy resin in which a filler such as alumina and zirconia is dispersed, and rubber in which the above-described filler is dispersed.

The ultrasound transducer 7 having the above-described configuration irradiates the observation target with the ultrasound via the first acoustic matching layer 72, the second acoustic matching layer 73, the mask portion 74, and the acoustic lens 75 as the piezoelectric element 71 vibrates due to the input of the pulse signal. At this time, the vibration of the piezoelectric element 71 is attenuated by the backing material 76 and the vibration of the piezoelectric element 71 is not transmitted on the opposite side to a side of the piezoelectric element 71, the side where the first acoustic matching layer 72, the second acoustic matching layer 73, the mask portion 74, and the acoustic lens 75 are arranged. In addition, the ultrasound reflected from the observation target is transmitted to the piezoelectric element 71 via the acoustic lens 75, the mask portion 74, the second acoustic matching layer 73, and the first acoustic matching layer 72. The piezoelectric element 71 vibrates due to the transmitted ultrasound, the piezoelectric element 71 converts the vibration into the electrical echo signal, and outputs the echo signal to the ultrasound observation apparatus 3 via a wiring (not illustrated).

Figure 10:
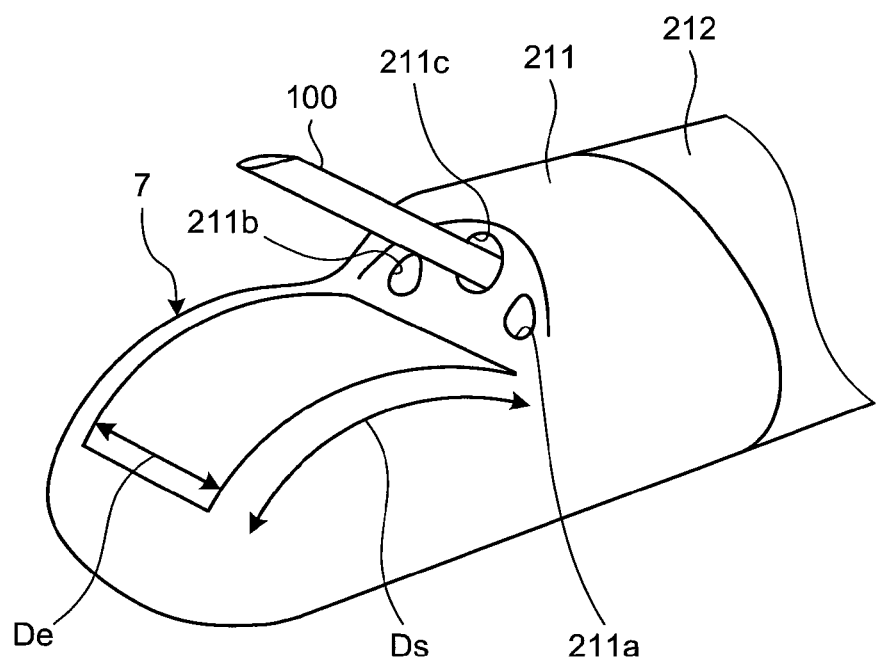
FIG. 10 is a perspective view schematically illustrating a configuration of the distal end of the insertion portion of the ultrasound endoscope according to the first embodiment of the present invention.

Next, reference will be made to a method for detecting a protruding direction of a puncture needle using the above-described ultrasound transducer 7. FIG. 10 is a perspective view schematically illustrating a configuration of the distal end of the insertion portion of the ultrasound endoscope according to the first embodiment. When a puncture needle 100 is used as the treatment tool, the puncture needle 100 is inserted into the insertion portion 21 through the treatment tool insertion port 223 (see FIG. 1), and a distal end of the puncture needle 100 is caused to protrude from the treatment tool protrusion port 211c. Accordingly, the distal end of the puncture needle 100 is positioned inside a scanning region of the ultrasound transducer 7, and a part of interest is punctured by the puncture needle 100 while confirming whether the puncture needle 100 protrudes through an ultrasound image.

However, the ultrasound image is a sectional image which is parallel to the scanning direction Ds, and it is difficult to grasp a position of the puncture needle 100 in the elevation direction De. Although it is possible to confirm a protruding position of the puncture needle 100 in the scanning direction Ds through the ultrasound image, it is difficult to confirm bending of the puncture needle 100 in the elevation direction De.

Figure 11:
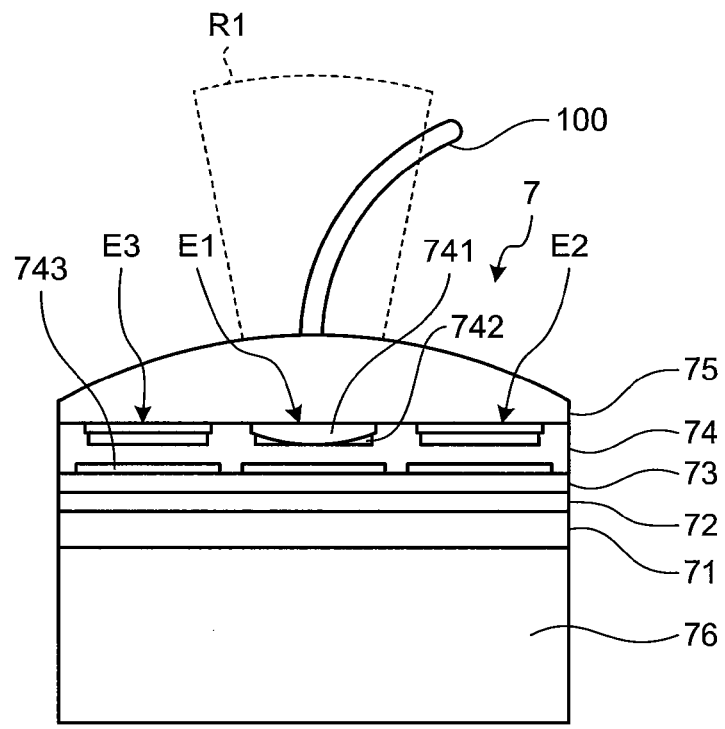
FIG. 11 is a diagram for describing a position relationship between a scanning range of the ultrasound transducer and a puncture needle according to the first embodiment of the present invention.

Hereinafter, reference will be made to a method for detecting the position of the puncture needle 100 in the elevation direction in the ultrasound transducer 7 according to the first embodiment. FIG. 11 is a diagram for describing a position relationship between a scanning range of the ultrasound transducer and the puncture needle according to the first embodiment. In FIG. 11, the counter electrode 743 in the divided region E1 is electrically charged, and scanning in a scanning region R1 is performed using ultrasound passed through the divided region E1. In FIG. 11, the counter electrode 743 in the divided regions E2 and E3 is not electrically charged, and thus, the ultrasound is reflected from the respective hollow portions 742 and does not reach the acoustic lens 75. In this case, ultrasound scanning is performed in a central portion in the elevation direction De. Thus, when a longitudinal direction of the puncture needle 100 is bent with respect to a plane parallel to the scanning direction Ds, the distal end of the puncture needle 100 deviates from the scanning region R1 as illustrated in FIG. 11.

Figure 12:
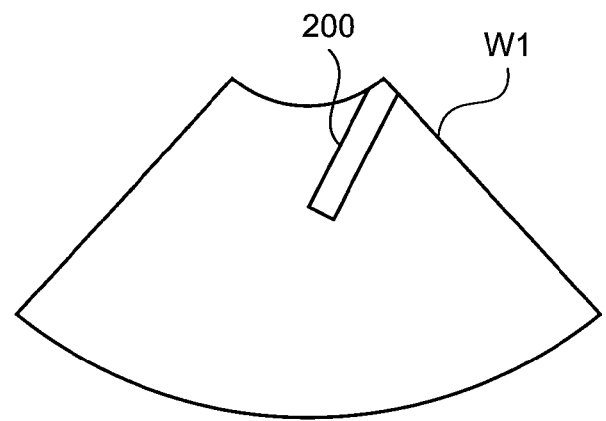
FIG. 12 is a diagram schematically illustrating an ultrasound image that is obtained by scanning of the ultrasound transducer illustrated in FIG. 11.

FIG. 12 is a diagram schematically illustrating an ultrasound image that is obtained by scanning of the ultrasound transducer illustrated in FIG. 11. An ultrasound image W1 illustrated in FIG. 12 is an image that is obtained by the ultrasound scanning illustrated in FIG. 11, and is an image showing a case where the distal end of the puncture needle 100 side deviates from the scanning region R1 as described above. When the distal end of the puncture needle 100 deviates from the scanning region R1, an image (needle image 200) of the puncture needle 100 present inside the scanning region R1 is present in the ultrasound image W1 as illustrated in FIG. 12.

Figure 13:
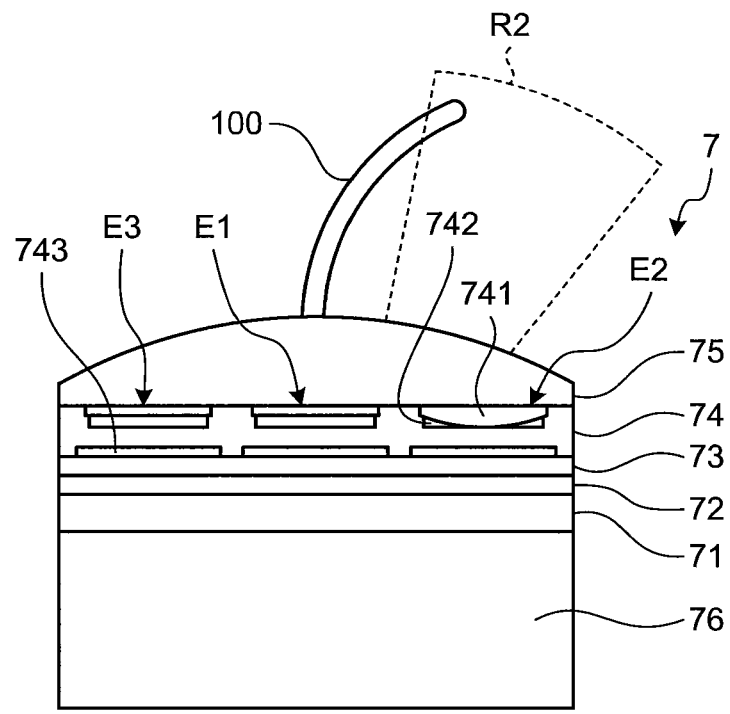
FIG. 13 is a diagram for describing a position relationship between the scanning range of the ultrasound transducer and the puncture needle according to the first embodiment of the present invention.

FIG. 13 is a diagram for describing a position relationship between the scanning range of the ultrasound transducer and the puncture needle according to the first embodiment. A bending state of the puncture needle 100 with respect to the ultrasound transducer 7 is the same as that of FIG. 11. In FIG. 13, the counter electrode 743 in the divided region E2 is electrically charged, and scanning in a scanning region R2 is performed using ultrasound passed through the divided region E2. In FIG. 13, the counter electrode 743 in the divided regions E1 and E3 is not electrically charged, and thus, the ultrasound is reflected from the respective hollow portions 742 and does not reach the acoustic lens 75. In this case, ultrasound scanning is performed in one end portion in the elevation direction De. Thus, when the longitudinal direction of the puncture needle 100 is bent with respect to the plane parallel to the scanning direction Ds, only the distal end of the puncture needle 100 is positioned inside the scanning region R2 as illustrated in FIG. 13.

Figure 14:
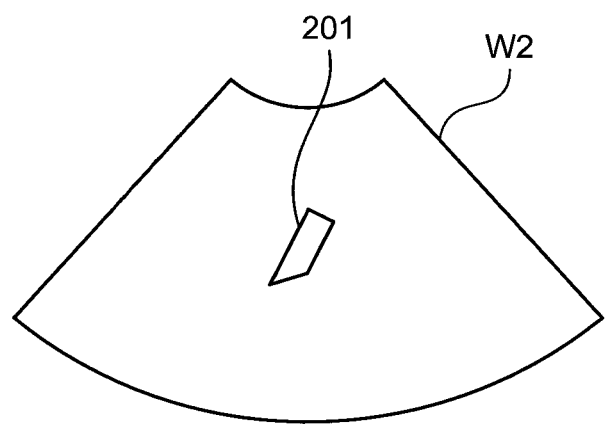
FIG. 14 is a diagram schematically illustrating an ultrasound image that is obtained by scanning of the ultrasound transducer illustrated in FIG. 13.

FIG. 14 is a diagram schematically illustrating an ultrasound image that is obtained by scanning of the ultrasound transducer illustrated in FIG. 13. An ultrasound image W2 illustrated in FIG. 14 is an image that is obtained by the ultrasound scanning illustrated in FIG. 13, and is an image showing a case where only the distal end of the puncture needle 100 side is positioned inside the scanning region R2 as described above. When only the distal end of the puncture needle 100 is positioned inside the scanning region R2, an image (needle image 201) of the puncture needle 100 present inside the scanning region R2 is present in the ultrasound image W2 as illustrated in FIG. 14.

Figure 15:
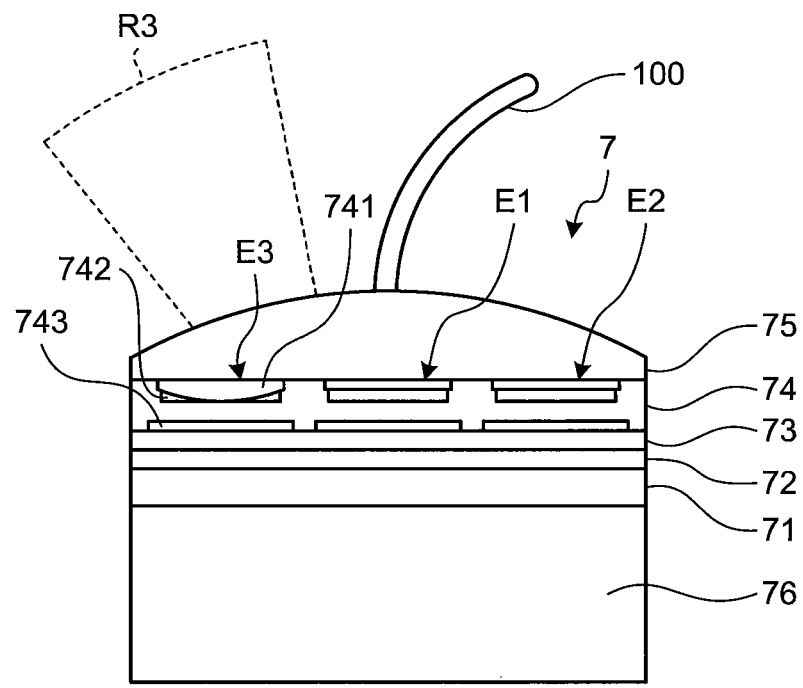
FIG. 15 is a diagram for describing a position relationship between the scanning range of the ultrasound transducer and the puncture needle according to the first embodiment of the present invention.

FIG. 15 is a diagram for describing a position relationship between the scanning range of the ultrasound transducer and the puncture needle according to the first embodiment of the present invention. A bending state of the puncture needle 100 with respect to the ultrasound transducer 7 is the same as that of FIG. 11. In FIG. 15, the counter electrode 743 in the divided region E3 is electrically charged, and scanning in a scanning region R3 is performed using ultrasound passed through the divided region E3. In FIG. 15, the counter electrode 743 in the divided regions E1 and E2 is not electrically charged, and thus, the ultrasound is reflected from the respective hollow portions 742 and does not reach the acoustic lens 75. In this case, ultrasound scanning is performed in the other end portion in the elevation direction De. Thus, when the longitudinal direction of the puncture needle 100 is bent with respect to the plane parallel to the scanning direction Ds, the puncture needle 100 is positioned outside the scanning region R3 as illustrated in FIG. 15.

Figure 16:
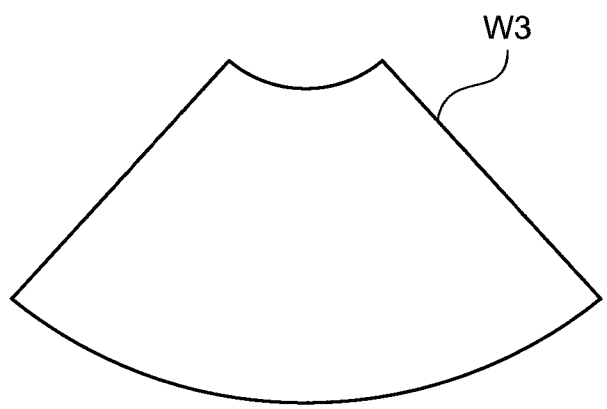
FIG. 16 is a diagram schematically illustrating an ultrasound image that is obtained by scanning of the ultrasound transducer illustrated in FIG. 15.

FIG. 16 is a diagram schematically illustrating an ultrasound image that is obtained by scanning of the ultrasound transducer illustrated in FIG. 15. An ultrasound image W3 illustrated in FIG. 16 is an image that is obtained by the ultrasound scanning illustrated in FIG. 15, and is an image showing a case where the puncture needle 100 side is positioned outside the scanning region R3 as described above. When the puncture needle 100 is positioned outside the scanning region R3, an image of the puncture needle 100 as an image of the scanning region R3 is not present in the ultrasound image W3 as illustrated in FIG. 16.

As described above, it is possible to obtain the ultrasound images of the scanning regions R1 to R3 corresponding to the divided regions E1 to E3 by adjusting the application of the charge to the counter electrode 743 in the divided regions E1 to E3. Each of the ultrasound images of the scanning regions R1 to R3 is an image that corresponds to a region obtained by dividing the elevation direction De. Thus, it is possible to detect the protruding direction of the puncture needle 100 by confirming the respective ultrasound images of the scanning regions R1 to R3 even when the puncture needle 100 is bent with respect to the plane parallel to the scanning direction Ds as described above. It is possible to more reliably puncture the part of interest by accurately detecting the protruding direction of the puncture needle 100. The detection and the like of the puncture needle may be performed by arbitrarily selecting two divided regions and acquiring ultrasound images of two scanning regions divided in the elevation direction De.

In contrast, an ultrasound image including all the scanning regions R1 to R3 is obtained in the conventional 1-D array ultrasound transducer. Thus, when the protruding direction of the puncture needle 100 is bent with respect to the plane parallel to the scanning direction Ds, it is difficult to determine a bending direction of the puncture needle 100.

According to the above-described first embodiment, the mask portion 74, capable of selectively controlling the passage of the ultrasound in the region obtained by dividing the elevation direction De depending on the application of the charge, is provided between the second acoustic matching layer 73 and the acoustic lens 75 in the ultrasound transducer 7. Thus, it is possible to obtain the plurality of ultrasound images taken along the elevation direction De with the simple configuration. According to the first embodiment, it is possible to the ultrasound image in the elevation direction while suppressing an increase in the number of wirings as compared to a 2-D array ultrasound transducer. Since the number of the wirings is suppressed, it is possible to downsize the ultrasound transducer as compared to the 2-D array ultrasound transducer.

In addition, it is possible to acquire an ultrasound image that visualizes even an image at a far point while improving resolution of a near point if a frequency (pulse interval of the pulse signal) to be applied to the ultrasound transducer 7 is set to a high frequency in the case of scanning only the central portion (scanning region R1) in the elevation direction De, and the frequency to be supplied to the ultrasound transducer 7 is set to a low frequency in the case of scanning the entire region (scanning regions R1 to R3) of the elevation direction De in the above-described first embodiment.

In addition, the electret portion 741 is formed using fluororesin such as Teflon (registered trademark) or polyethylene terephthalate according to the above-described first embodiment, and thus, can be manufactured at relatively low cost. Further, the electret portion 741 is bendable, and thus, it is possible to produce the mask portion 74 by deforming the mask portion 74 in a shape taken along a curved surface when it is necessary to perform the arrangement along the curved surface as in the convex-type ultrasound transducer, for example.

The 1-D array has been exemplified in the above-described first embodiment. However, the invention can be applied even in a 1.25-D array, a 1.5-D array, or a 1.75-D array in which a plurality of piezoelectric elements (oscillators) is arrayed in a direction (elevation direction) that is substantially orthogonal to the scanning direction of the ultrasound transducer (the array direction of the piezoelectric element in the 1-D array). The first embodiment includes the 1.25-D, 1.5-D and 1.75-D arrays in which a single ultrasound image, divided in the elevation direction De, is acquired in the scanning direction Ds, as the array obtained by one-dimensionally arraying the plurality of piezoelectric elements.

Modified Example of First Embodiment

Figure 17:
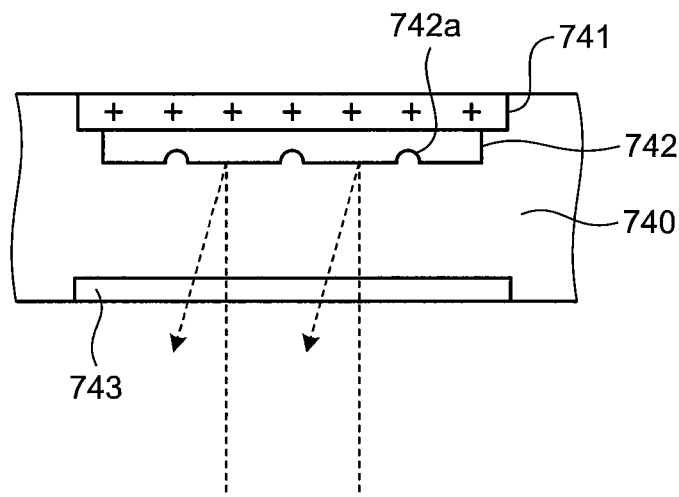
FIG. 17 is a diagram for describing a configuration of an ultrasound transducer according to a modified example of the first embodiment of the present invention.

FIG. 17 is a diagram for describing a configuration of an ultrasound transducer according to a modified example of the first embodiment of the present invention and illustrating a state in which the counter electrode 743 has no charge. In the modified example, a plurality of convex portions 742a is provided in the hollow portion 742 according to the above-described first embodiment. As illustrated in FIG. 17, the convex portion 742a protruding in the substantially orthogonal direction from a bottom surface opposing the electret portion 741 is provided in the hollow portion 742 of the mask portion 74 according to the modified example. The convex portion 742a can protrude from the bottom surface and also can be flush with the bottom surface, and abuts on the surface of the electret portion 741 in the most protruding state. When the counter electrode 743 has no charge, the electret portion 741 is supported by the convex portions 742a.

Figure 18:
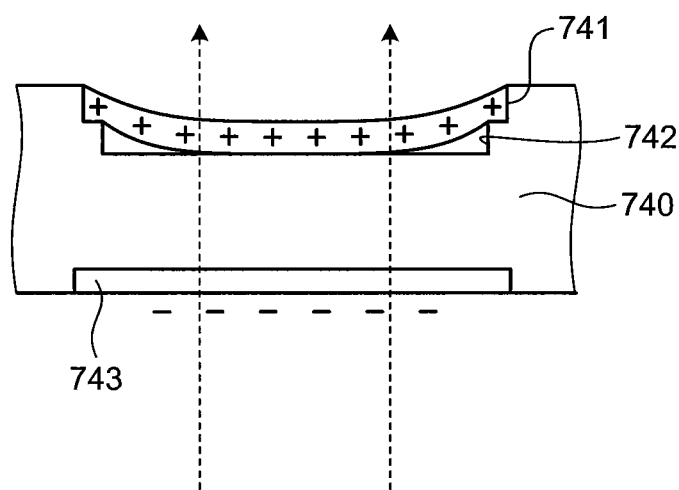
FIG. 18 is a diagram for describing the configuration of the ultrasound transducer according to the modified example of the first embodiment of the present invention.

FIG. 18 is a diagram for describing the configuration of the ultrasound transducer according to the modified example of the first embodiment of the present invention and illustrating a state in which the counter electrode 743 is electrically charged. The mask portion 74 allows ultrasound to pass when the counter electrode 743 is electrically charged since the electret portion 741 is attracted to the counter electrode 743 which has been negatively charged, to enter into the hollow portion 742 and be brought into contact with the bottom of the hollow portion 742 as illustrated in FIG. 18. At this time, the convex portion 742a is flush with the bottom surface, which does not hinder the contact between the bottom surface of the hollow portion 742 and the electret portion 741.

Since the convex portion 742a is provided in the hollow portion 742 according to the modified example, the convex portion 742a supports the electret portion 741 in the state in which the counter electrode 743 has no charge, and thus, it is possible to more reliably form the hollow space between the electret portion 741 and the hollow portion 742. Although the electret portion 741 needs to have a certain degree of bendability, when the convex portion 742a is provided, it is possible to suppress the contact between the electret portion 741 and the bottom surface of the hollow portion 742 using the convex portion 742a even in a case where the electret portion 741 is bent toward the hollow portion 742 side due to its own weight. Further, it is possible to more reliably perform the blocking of the ultrasound through the hollow portion 742.

Second Embodiment

Figure 19:
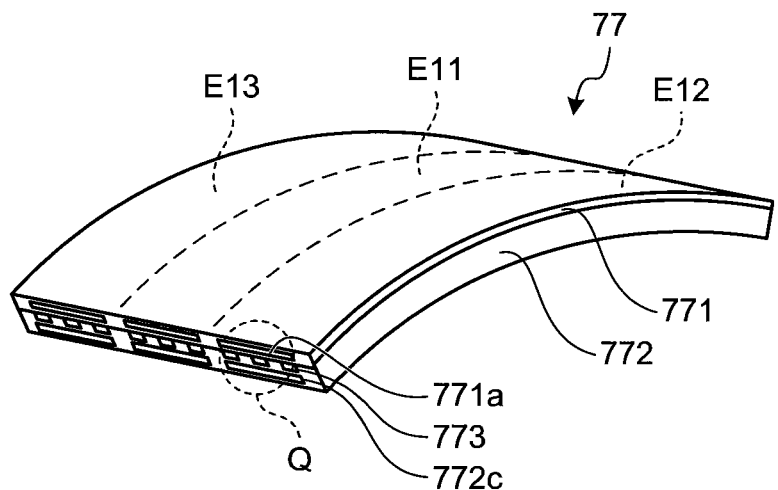
FIG. 19 is a schematic diagram illustrating a configuration of main parts of an ultrasound transducer according to a second embodiment of the present invention.

FIG. 19 is a schematic diagram illustrating a configuration of main parts of an ultrasound transducer according to a second embodiment of the present invention. Although, in the above-described first embodiment, the electret is used as the mask portion 74, a capacitive micromachined ultrasonic transducer (C-MUT) is used as a mask portion 77 in the second embodiment.

The mask portion 77 has a sheet shape that is formed using a material that allows ultrasound to pass therethrough, and is provided between the second acoustic matching layer 73 and the acoustic lens 75. The mask portion 77 is formed by stacking a first sheet 771 having a sheet shape that is bendable and a second sheet 772 having a sheet shape. The first sheet 771 and the second sheet 772 are formed using a silicon film, for example. The first sheet 771 includes three first electrodes 771a each of which has a rectangular shape. The second sheet 772 includes a plurality of protruding portions 772b, each of which protrudes from a surface 772a facing the first sheet 771 (see FIG. 20), and three second electrodes 772c, each of which faces the first electrode 771a and has a rectangular shape. In the mask portion 77, the first sheet 771 is supported by the protruding portions 772b to form a plurality of hollow portions 773 having strip-shaped hollow spaces. The hollow portion 773 is filled with gas (air).

The mask portion 77 having the above-described configuration forms a configuration of the capacitive micromachined ultrasonic transducer (C-MUT) which has a cavity (hollow space) between two electrode layers. In other words, the mask portion 77 includes one or more hollow portions 773 between three pairs of the first electrode 771a and the second electrode 772c. In the mask portion 77, the first electrode 771a and the second electrode 772c are connected to each other via an electric circuit (not illustrated), and an electrostatic force acts between the first electrode 771a and the second electrode 772c when a DC voltage is applied between the first electrode 771a and the second electrode 772c so that the first sheet 771 (the first electrode 771a) is attracted to the second sheet 772 (the second electrode 772c) side.

The mask portion 77 causes the hollow space present on a traveling direction of ultrasound to be filled and turned into a collapse state when the DC voltage is applied to any of the three pairs of the first electrode 771a and the second electrode 772c, thereby enabling the passage of the ultrasound. To be specific, when three mask structures of the first electrode 771a, the second electrode 772c, and the hollow portion 773 are arrayed in the elevation direction De in the ultrasound transducer 7, the mask portion 77 divides the region to be masked into three regions in the elevation direction De (divided regions E11 to E13). When a DC voltage is applied between the first electrode 771a and the second electrode 772c in any divided region among the three divided regions E11 to E13, the first sheet 771 is brought into contact with the surface 772a of the second sheet 772 such that first sheet 771 is buried in the hollow portion 773, thereby allowing the ultrasound to pass in the divided region. For example, when a DC voltage is applied between the first electrode 771a and the second electrode 772c in the divided region E11, the ultrasound is emitted only from the divided region E11.

Figure 20:
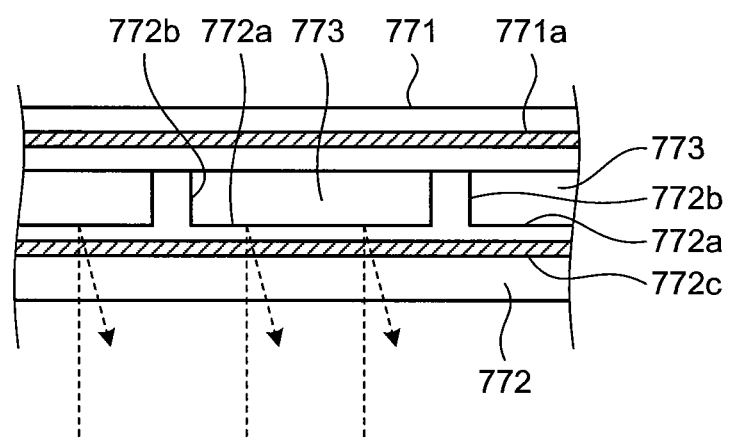
FIG. 20 is a diagram for describing propagation of ultrasound in the ultrasound transducer according to the second embodiment of the present invention.
Figure 21:
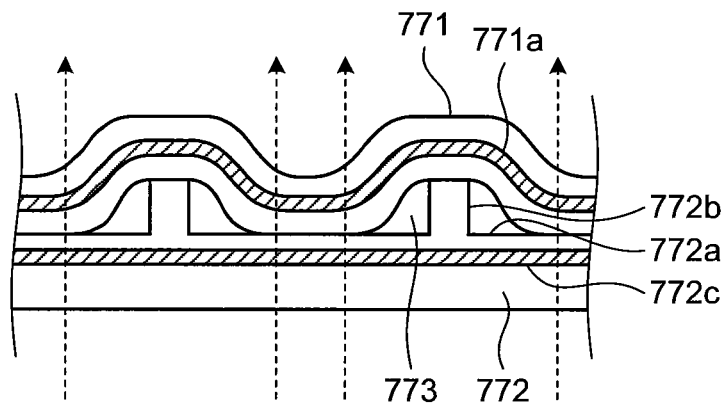
FIG. 21 is a diagram for describing propagation of ultrasound in the ultrasound transducer according to the second embodiment of the present invention.

Here, masking processing performed by the mask portion 77 of the ultrasound transducer 7 will be described with reference to FIGS. 20 and 21. FIG. 20 is a diagram for describing propagation of ultrasound in the ultrasound transducer according to the second embodiment and illustrating a state in which a DC voltage is not applied between the first electrode 771a and the second electrode 772c. FIG. 21 is a diagram for describing propagation of ultrasound in the ultrasound transducer according to the second embodiment and illustrating a state in which a DC voltage is applied between the first electrode 771a and the second electrode 772c. FIGS. 20 and 21 are diagrams obtained by enlarging a region Q illustrated in FIG. 19.

The mask portion 77 blocks the passage of the ultrasound using the hollow portion 773 between the first sheet 771 and the second sheet 772 when the DC voltage is not applied between the first electrode 771a and the second electrode 772c as illustrated in FIG. 20 (a dashed arrow in FIG. 20).

When the DC voltage is applied between the first electrode 771a and the second electrode 772c in the mask portion 77, the electrostatic force acts between the first electrode 771a and the second electrode 772c, and the first sheet 771 enters into the hollow portion 773 and is brought into contact with the surface 772a of the second sheet 772, and thus, the ultrasound passes therethrough as illustrated in FIG. 21 (a dashed arrow in FIG. 21).

In this manner, the passage of the ultrasound using the mask portion 77 is controlled by the application of the DC voltage to the portion between the first electrode 771a and the second electrode 772c. It is possible to emit the ultrasound from a desired region by controlling the application of the DC voltage to the divided regions E11 to E13. In addition, conversely, it is possible to control a reception region of the ultrasound echo by the application of the charge.

According to the above-described second embodiment, the mask portion 77, capable of selectively controlling the passage of the ultrasound in the region obtained by dividing the elevation direction De depending on the application of the charge, is provided between the second acoustic matching layer 73 and the acoustic lens 75 in the ultrasound transducer 7. Thus, it is possible to obtain the plurality of ultrasound images taken along the elevation direction De with the simple configuration, which is similar to the above-described first embodiment.

In addition, the configuration of the capacitive micromachined ultrasonic transducer (C-MUT) in which the cavity is provided between the two electrode layers in the mask portion 77 is used according to the second embodiment, and thus, it is possible to control the passage of the ultrasound or the blocking of the passage at high speed.

Modified Example of Second Embodiment

Figure 22:
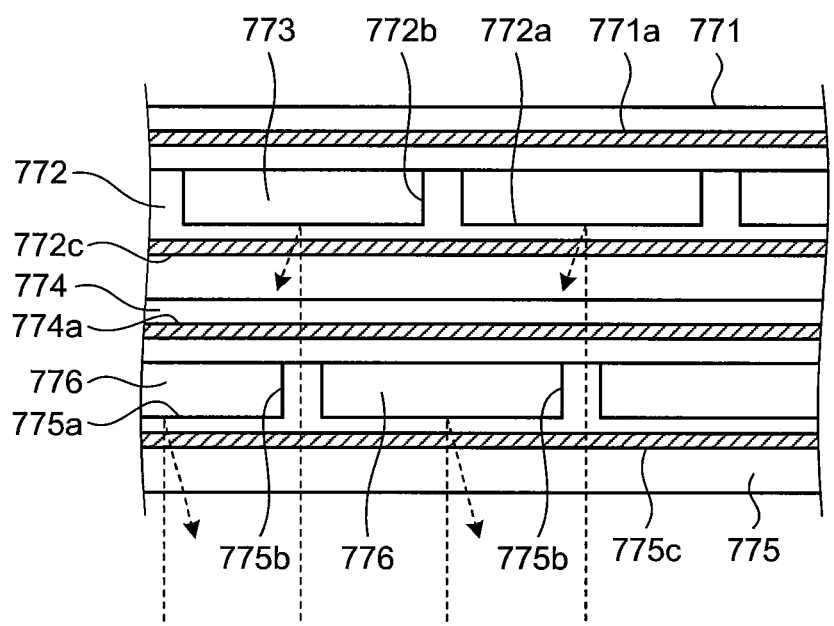
FIG. 22 is a diagram for describing a configuration of main parts of an ultrasound transducer according to a modified example of the second embodiment of the present invention.

FIG. 22 is a diagram for describing a configuration of main parts of an ultrasound transducer according to a modified example of the second embodiment of the present invention and illustrating a state in which a DC voltage is not applied between electrodes. In the above-described second embodiment, there is a case where ultrasound passes through the protruding portion 772b since the first sheet 771 and the protruding portion 772b are in the state of being contact with each other even in the state where the DC voltage is not applied between the first electrode 771a and the second electrode 772c. In the modified example, a third sheet 774 and a fourth sheet 775 are stacked onto the first sheet 771 and the second sheet 772 so as to prevent the ultrasound from passing through the protruding portion 772b.

To be specific, the first sheet 771, the second sheet 772, the third sheet 774, and the fourth sheet 775 are stacked in this order as illustrated in FIG. 22. The third sheet 774 and the fourth sheet 775 are formed using a silicon film, for example. The third sheet 774 includes three third electrodes 774a, each of which has a rectangular shape. The fourth sheet 775 includes a plurality of protruding portions 775b, each of which protrudes from a surface 775a facing the third sheet 774, and three fourth electrodes 775c, each of which faces the third electrode 774a and has a rectangular shape.

In the mask portion according to the modified example, the third sheet 774 is supported by the protruding portions 775b to form a plurality of hollow portions 776 having strip-shaped hollow spaces.

In the modified example, the protruding portion 775b is provided at a position not to overlap the protruding portion 772b in the propagation direction of the ultrasound when the first sheet 771, the second sheet 772, the third sheet 774, and the fourth sheet 775 are stacked. In other words, the protruding portions 772b and 775b are arranged at positions different from each other when being viewed from a direction orthogonal to the propagation direction of the ultrasound. Accordingly, when ultrasound is incident from the fourth sheet 775, passage of the ultrasound passing through the protruding portion 775b outside the mask portion 77 is blocked by the hollow portion 773 as illustrated in FIG. 22, for example. Since the passage of the ultrasound is blocked by the hollow portion 776, the ultrasound does not reach the protruding portion 772b. In addition, it is possible to cause the ultrasound to pass outside the mask portion 77 by applying a DC voltage to each portion between the respective electrodes.

Third Embodiment

Figure 23:
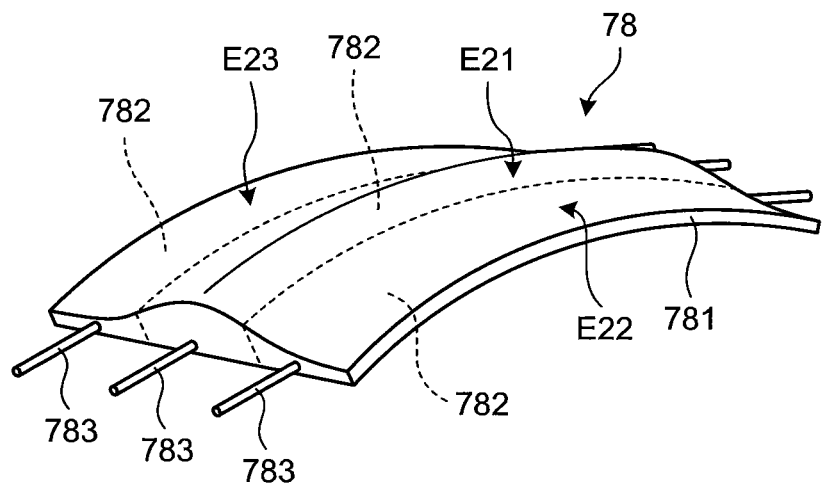
FIG. 23 is a schematic diagram illustrating a configuration of main parts of an ultrasound transducer according to a third embodiment of the present invention.
Figure 24:
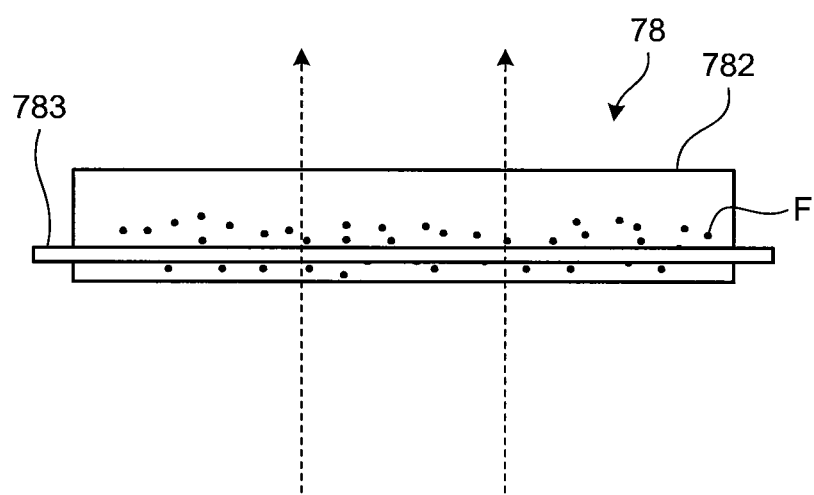
FIG. 24 is a diagram for describing propagation of ultrasound in the ultrasound transducer according to the third embodiment of the present invention.
Figure 25:
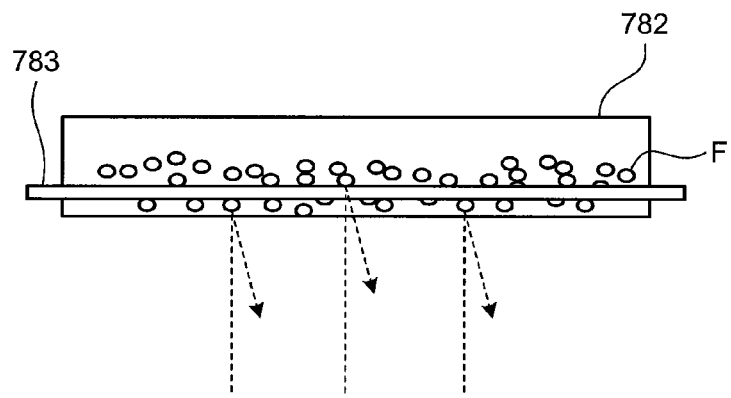
FIG. 25 is a diagram for describing propagation of ultrasound in the ultrasound transducer according to the third embodiment of the present invention.

FIG. 23 is a schematic diagram illustrating a configuration of main parts of an ultrasound transducer according to a third embodiment of the present invention. FIGS. 24 and 25 are diagrams for describing propagation of ultrasound in the ultrasound transducer according to the third embodiment. In the third embodiment, a foam material is provided on a propagation path of ultrasound to block passage of the ultrasound. In the third embodiment, a mask portion is provided in an acoustic lens 78.

The acoustic lens 78 is formed using silicone, polymethylpentene, epoxy resin, polyetherimide, or the like, and includes a lens main body 781 whose one surface is formed in a convex shape or a concave shape and has a function of narrowing the ultrasound. The lens main body 781 is provided with three mixed portions 782 that are mixed with a material F which expands with heat. In the lens main body 781, an electric heating wire 783, which penetrates through the mixed portion 782 and is connected to an electric circuit (not illustrated), is provided for each of the mixed portions 782. The material F reversibly reacts, expands by heating and contracts when the heating is stopped. In the third embodiment, the mask portion is configured using the mixed portion 782 including the material F and the electric heating wire 783. The mask portion according to the third embodiment is provided between the piezoelectric element 71 and a radiation surface of the ultrasound (a surface of the acoustic lens 78).

In the acoustic lens 78 having the above-described configuration, ultrasound passes through the material F when an AC voltage is not applied to the electric heating wire 783 as illustrated in FIG. 24. In contrast, heat is generated when the AC voltage is applied to the electric heating wire 783 (by power supply), and the generated heat is transmitted to the material F. When the heat is transmitted to the material F, the material F expands as illustrated in FIG. 25, thereby blocking passage of the ultrasound. To be specific, when a mask structure corresponding to the mixed portion 782 including the material F is arrayed in the elevation direction De in the ultrasound transducer 7, the acoustic lens 78 (mask portion) divides a region to be masked into three regions in the elevation direction De (divided regions E21 to E23). When an AC voltage is applied to the electric heating wire 783 in any divided region among the three divided regions E21 to E23, air bubbles are generated inside the mixed portion 782 in the region, and the passage of the ultrasound is blocked. For example, when an AC voltage is applied to the electric heating wire 783 corresponding to the divided regions E22 and E23, the ultrasound is emitted only from the divided region E21. It is preferable to prevent the transmission of heat to the adjacent mixed portion 782 among the respective mixed portions 782.

According to the above-described third embodiment, it is possible to select the ultrasound to be emitted from the divided regions E21 to E23 by providing the three mixed portions 782, which contains the material F expanding by heat, inside the acoustic lens 78 so as to control the heating of the material F using the electric heating wires 783 that pass through the respective mixed portions 782 in the ultrasound transducer 7. Thus, it is possible to obtain the plurality of ultrasound images taken along the elevation direction De with the simple configuration, which is similar to the above-described first embodiment.

In addition, it is configured only by mixing the material F, which expands by heat, in a predetermined region of the acoustic lens 78 and providing the electric heating wire 783 according to the third embodiment, thus, it is unnecessary to form the hollow portion 742 and the like described above, and it is possible to easily produce the ultrasound transducer.

Fourth Embodiment

Figure 26:
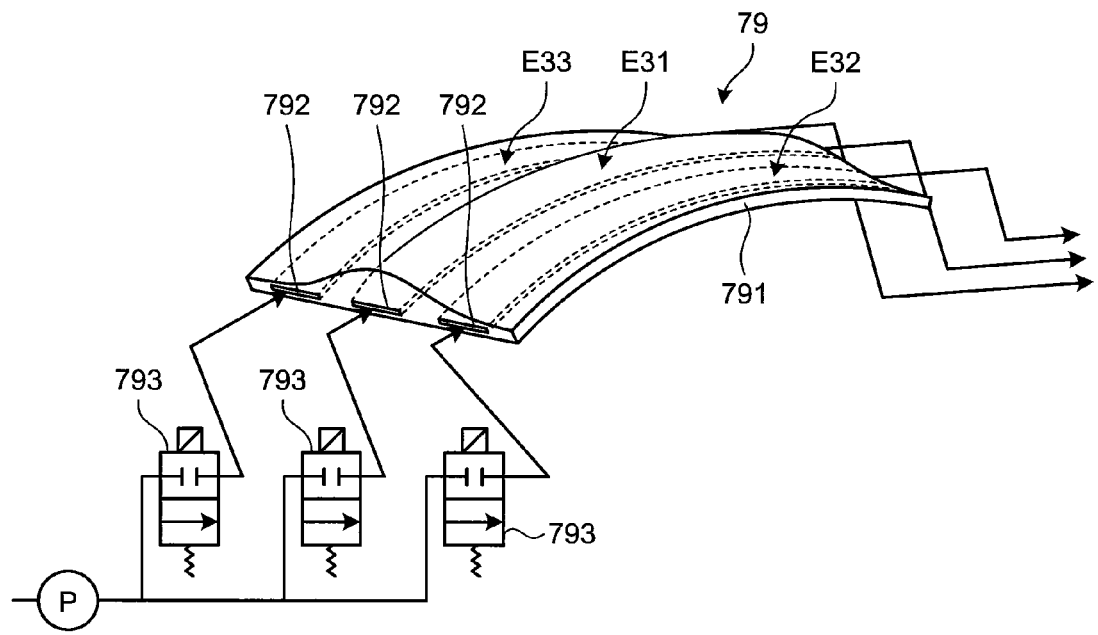
FIG. 26 is a schematic diagram illustrating a configuration of main parts of an ultrasound transducer according to a fourth embodiment of the present invention.
Figure 27:
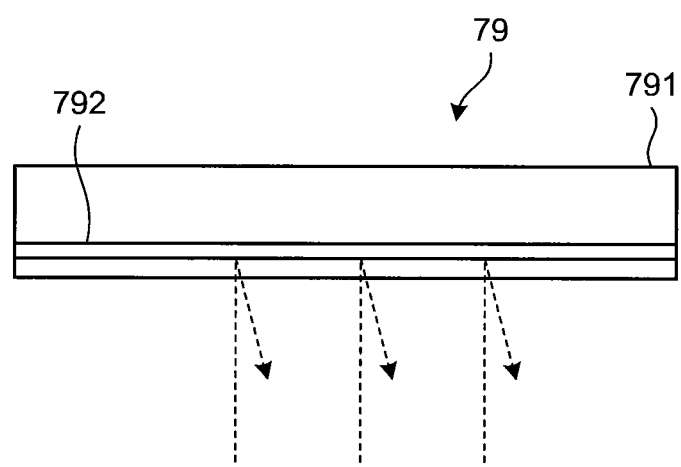
FIG. 27 is a diagram for describing propagation of ultrasound in the ultrasound transducer according to the fourth embodiment of the present invention.

FIG. 26 is a schematic diagram illustrating a configuration of main parts of an ultrasound transducer according to a fourth embodiment of the present invention. FIG. 27 is a diagram for describing propagation of ultrasound in the ultrasound transducer according to the fourth embodiment. In the fourth embodiment, it is configured to have a structure that includes an acoustic lens 79 that reversibly performs passage and blocking of ultrasound by providing a space through which a fluid flows on a propagation path of the ultrasound.

The acoustic lens 79 is formed using silicone, polymethylpentene, epoxy resin, polyetherimide, or the like, and includes a lens main body 791 whose one surface is formed in a convex shape or a concave shape and has a function of narrowing the ultrasound. The lens main body 791 is provided with three hollow portions 792 which extend in parallel with each other and form strip-shaped hollow spaces. The fluid that is capable of propagating ultrasound, for example, water can flow through the hollow portion 792 via a pump and an electromagnetic valve 793. In the fourth embodiment, a mask portion is configured using the hollow portion 792 and the fluid that is inserted through the hollow portion 792. The mask portion according to the fourth embodiment is provided between the piezoelectric element 71 and a radiation surface of the ultrasound (a surface of the acoustic lens 79).

In the acoustic lens 79 having the above-described configuration, the passage of the ultrasound is blocked when the fluid does not flow through the hollow portion 792 as illustrated in FIG. 27. In contrast, when the fluid is caused to flow through the hollow portion 792, the ultrasound passes through the fluid and is emitted from the acoustic lens 79 to the outside. To be specific, when a mask structure corresponding to the hollow portion 792 is arrayed in the elevation direction De in the ultrasound transducer 7, the acoustic lens 79 (mask portion) divides a region to be masked into three regions in the elevation direction De (divided regions E31 to E33). When a fluid is caused to flow through the hollow portion 792 in any divided region among the three divided regions E31 to E33, the fluid flowing through the hollow portion 792 in the region causes the ultrasound to pass therethrough. For example, when a fluid is caused to flow only through the hollow portion 792 corresponding to the divided region E31, the ultrasound is emitted only from the divided region E31.

According to the above-described fourth embodiment, it is possible to select the ultrasound to be emitted from the divided regions E31 to E33 by providing the three hollow portions 792, which enables the fluid capable of propagating the ultrasound such as water to flow therethrough, inside the acoustic lens 79 so as to control the fluid caused to flow through the hollow portion 792 in the ultrasound transducer 7. Thus, it is possible to obtain the plurality of ultrasound images taken along the elevation direction De with the simple configuration, which is similar to the above-described first embodiment.

In addition, the fluid is caused to flow through the inside of the acoustic lens 79 according to the fourth embodiment, and thus, an effect of suppressing heat dissipation from the acoustic lens 79 is achieved as the fluid absorbs the heat generated, for example, in the ultrasound transducer 7, and particularly in the acoustic lens 79.

Although, in the above-described third and fourth embodiments, the mask portion is provided in the acoustic lens, the above-described mask portion may be provided on a different sheet from the acoustic lens to be arranged, for example, between the second acoustic matching layer and the acoustic lens as in the first and second embodiments.

The modes for carrying out the present invention have been described hereinbefore. However, the present invention is not limited only to the embodiments and the modified examples described above. The present invention may include various embodiments within a range that does not depart from the technical ideas described in the claims without being not limited to the embodiments and the modified example described above. In addition, each configuration of the embodiments and the modified examples may be appropriately combined.

In the above-described first to fourth embodiments and the modified examples, the three divided regions are obtained in the elevation direction. However, the respective divided regions may be obtained by performing the division evenly, may be provided such that the central portion is larger than both end portions, or may be different from each other. In addition, the number of the divided regions is not limited to three but may be two, and four or more divided regions may be provided.

A slim ultrasound miniature probe without an optical system may be applied as the ultrasound probe. The ultrasound miniature probe is generally used to be inserted into a biliary tract, a biliary duct, a pancreatic duct, a trachea, a bronchial tube, a urethra, or a ureter to examine adjacent organs thereof (a pancreas, a lung, a prostate, a bladder, a lymph node, or the like).

An external ultrasound probe for emitting ultrasound from a body surface of a subject may be applied as the ultrasound probe. The external ultrasound probe is generally used to observe an abdominal organ (a liver, a gallbladder, or a bladder), a breast (especially, a mammary gland), and a thyroid.

According to some embodiments, it is possible to obtain a plurality of ultrasound images taken along an elevation direction with a simple configuration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound transducer for irradiating a subject with ultrasound and receiving an ultrasound echo reflected from the subject, the ultrasound transducer comprising:
   a plurality of piezoelectric elements configured to emit ultrasound according to input of an electric signal and convert ultrasound incident from outside into an electric signal; and
   a mask provided between the plurality of piezoelectric elements and a radiation surface of the ultrasound on the ultrasound transducer, the mask being configured to:
      mask any divided region among a plurality of divided regions obtained by dividing an elevation direction orthogonal to a plane parallel to a scanning direction of the ultrasound;
      reflect the ultrasound in a direction different from a propagation direction of the ultrasound on the masked division region; and
      allow the ultrasound to pass in the propagation direction in the plurality of divided regions except the masked divided region;
   wherein the mask comprises:
      a plurality of electret portions arrayed along the elevation direction and configured to maintain electric polarization to generate an electric field;
      a plurality of hollow portions each forming a strip-shaped hollow space in accordance with arrangement of each of the plurality of electret portions; and
      a plurality of counter electrodes facing the plurality of electret portions and each having a strip shape.

2. The ultrasound transducer according to claim 1, wherein the plurality of piezoelectric elements is one-dimensionally arrayed.

3. The ultrasound transducer according to claim 1, further comprising:
   an acoustic matching layer configured to perform acoustic impedance matching between the plurality of piezoelectric elements and an observation target; and
   an acoustic lens configured to emit the ultrasound passed through the mask to outside,
   wherein the acoustic lens is stacked on the mask, the mask is stacked on the acoustic matching layer, and the acoustic matching layer is stacked on the plurality of piezoelectric elements.

4. An ultrasound probe comprising the ultrasound transducer according to claim 1 at a distal end of the ultrasound probe.

5. The ultrasound probe according to claim 4, wherein
   the ultrasound probe is an ultrasound endoscope comprising an insertion portion, and
   the insertion portion has the ultrasound transducer at a distal end of the insertion portion and is configured to be inserted into the subject.

* * * * *